(12) United States Patent
Hepler et al.

(10) Patent No.: US 11,375,717 B2
(45) Date of Patent: *Jul. 5, 2022

(54) COMBINATIONS OF ACARICIDES AND INSECT GROWTH REGULATORS FOR CONTROL OF FLEAS WITHOUT EMESIS IN ANIMALS

(71) Applicant: Piedmont Animal Health Inc., Greensboro, NC (US)

(72) Inventors: Douglas Hepler, Greensboro, NC (US); Roland Johnson, Greensboro, NC (US); Gail Dempsey, Greensboro, NC (US); Michael Kelly, Greensboro, NC (US)

(73) Assignee: Piedmont Animal Health Inc., Greensboro, NC (US)

( * ) Notice: Subject to any disclaimer, the term of this patent is extended or adjusted under 35 U.S.C. 154(b) by 27 days.

This patent is subject to a terminal disclaimer.

(21) Appl. No.: 16/984,898

(22) Filed: Aug. 4, 2020

(65) Prior Publication Data

US 2020/0359624 A1    Nov. 19, 2020

Related U.S. Application Data

(62) Division of application No. 15/938,861, filed on Mar. 28, 2018, now Pat. No. 10,736,318.

(60) Provisional application No. 62/477,886, filed on Mar. 28, 2017.

(51) Int. Cl.
| | |
|---|---|
| *A01N 43/22* | (2006.01) |
| *A01N 47/34* | (2006.01) |
| *A61K 31/17* | (2006.01) |
| *A61K 31/7048* | (2006.01) |
| *A61K 9/00* | (2006.01) |
| *A61K 9/20* | (2006.01) |
| *A61K 9/48* | (2006.01) |

(52) U.S. Cl.
CPC ............ *A01N 43/22* (2013.01); *A01N 47/34* (2013.01); *A61K 9/0056* (2013.01); *A61K 9/2009* (2013.01); *A61K 9/2054* (2013.01); *A61K 9/485* (2013.01); *A61K 9/4866* (2013.01); *A61K 31/17* (2013.01); *A61K 31/7048* (2013.01); *A01N 2300/00* (2013.01); *A61K 2300/00* (2013.01)

(58) Field of Classification Search
CPC .... A01N 43/22; A01N 47/34; A01N 2300/00; A61K 9/0056; A61K 9/2009; A61K 9/2054; A61K 9/485; A61K 9/4866; A61K 31/17; A61K 31/7048; A61K 2300/00
USPC ......................................................... 514/29
See application file for complete search history.

(56) References Cited

U.S. PATENT DOCUMENTS

| | | | |
|---|---|---|---|
| 9,220,719 B2 | 12/2015 | Riggs et al. | |
| 10,736,318 B2* | 8/2020 | Hepler | A01N 43/22 |
| 2003/0139459 A1 | 7/2003 | Tinembart et al. | |
| 2009/0156399 A1 | 6/2009 | Hungenberg et al. | |
| 2009/0325892 A1* | 12/2009 | Huang | A01N 47/40 |
| | | | 514/28 |
| 2010/0197620 A1 | 8/2010 | Lowe et al. | |
| 2015/0119432 A1 | 4/2015 | Nishiguchi et al. | |

FOREIGN PATENT DOCUMENTS

CN          101380004 B       10/2011

OTHER PUBLICATIONS

Singh et al.: "Chemotherapeutics for control and treatment of Ectoparasites in Companion animals". Intas Polivet (2013) vol. 14 (II): 257-263: (Year: 2013).
Hayes, B. et al.: "Field Evaluation of the Efficacy and Safety of a Combination of Spinosad and Treatment of Intestinal Nematode Infections in Dogs in Europe", Veterinary Parasitology 2015, vol. 207, pp. 99-106.
International Search Report dated Jun. 15, 2018, regarding PCT/US2018/024862.

* cited by examiner

*Primary Examiner* — Yih-Horng Shiao
(74) *Attorney, Agent, or Firm* — DLA Piper LLP (US)

(57) ABSTRACT

A single-dose oral formulation of spinosad and lufenuron and methods for its use in the extended control of a flea infestation on a domestic animal such as a dog without emesis.

11 Claims, No Drawings

COMBINATIONS OF ACARICIDES AND INSECT GROWTH REGULATORS FOR CONTROL OF FLEAS WITHOUT EMESIS IN ANIMALS

CROSS-REFERENCE TO RELATED APPLICATIONS

This application is a divisional application of U.S. application Ser. No. 15/938,861 filed Mar. 28, 2018, now issued as U.S. Pat. No. 10,736,318; which claims the benefit under 35 USC § 119(e) to U.S. Application Ser. No. 62/477,886 filed Mar. 28, 2017, now expired. The disclosure of each of the prior applications is considered part of and is incorporated by reference in the disclosure of this application.

BACKGROUND OF THE INVENTION

Field of the Invention

This invention provides a single-dose oral formulation of an acaricide and an insect growth regulator for the extended control of a flea infestation on a domestic animal (e.g., canine) without emesis. The invention also provides methods of using the formulation.

Background Information

Fleas are a major annoyance both for the animals they infest and people in their vicinity. Flea infestations can also lead to pathological conditions, such as flea-allergy dermatitis. Furthermore, economic expenses involved in flea control are high. In the United States, for example, pet owners spend over $1 billion dollars for flea control products annually.

Treatments currently available achieve varying degrees of success. Most treatments involve chemicals applied to indoor and outdoor surfaces, as well as to the pet. The chemicals used include a variety of carbamates, organophosphates, pyrethrins and pyrethroids. These compounds often have toxic side effects can be a problem for both the pet and its owner. Moreover, extended use of such compounds is leading to resistance among the flea population.

Lufenuron is the active ingredient in the veterinary flea control medication PROGRAM®, and one of the two active ingredients in the flea, heartworm, ringworm and anthelmintic medicine milbemycin oxime/lufenuron (SENTINEL®). Lufenuron is stored in the animal's body fat and transferred to adult fleas through the host's blood when they feed. Adult fleas transfer it to their growing eggs through their blood, and to hatched larvae feeding on their excrement. It does not kill adult fleas. The ordinary dose of lufenuron for flea control is 30 mg/kg in cats and 10 mg/kg in dogs. Emesis is a common side effect at both dosages.

The spinosyns (also known as A83453 factors) are agricultural insecticides that have shown activity against southern armyworm and other insects in the order Lepidoptera, and cotton aphid and other members of the order Homoptera. Spinosyns are naturally derived fermentation products that are produced by cultivation of *Saccharopolyspora spinosa*. The fermentation produces many factors, including spinosyn A and spinosyn D (also called A83543A and A8354D). Spinosyn A and spinosyn D are the two spinosyns that are most active as insecticides. A product comprised mainly of these two spinosyns is available commercially under the common name "spinosad" (see, e.g., U.S. Pat. No. 6,664,237), and is also sold in the United States under the name of COMFORTIS®, which is a tablet that kills fleas and prevents flea infestations on dogs for a month at a dose rate of 30 mg/kg and up to 60 mg/kg in smaller animals.

Like users of lufenuron in cats and dogs, users of COMFORTIS® spinosad find that their dogs experience emesis (vomiting) at a relatively high rate. The label for the product reports in excess of 12% of animals vomiting in response to a single instance of the drug's administration. Even after several months of use, acclimation is limited, with over 7% of animals still suffering from emesis, and a smaller percentage suffering other side effects.

Therefore, there exists a need for extended control of a flea infestation in domestic animals, especially dogs, without risk of emesis. Surprisingly, it has been found that spinosad, when administered with an insect growth regulator such as lufenuron, can achieve up to 100% efficacy against fleas in a single dose without causing vomiting in treated animals. The effect is not considered to be the result of synergy, but instead a novel path for both killing and controlling the growth of fleas at lower doses of spinosad than required for use of the active alone to provide a total control solution for a period of at least a month without risk of emesis.

SUMMARY OF THE INVENTION

The invention therefore provides a single-dose oral formulation of spinosad and lufenuron for the extended control of a flea infestation on an animal, such as a dog, that is suitable for administration once every 30 days (i.e., one month). The invention also provides methods of using the formulation of spinosad and lufenuron.

The formulation may be orally administered to an animal once per month and maintain systemic efficacy for the entirety of the treatment period. The present invention may be orally administered as a tablet at a single dosage, including as a chewable tablet, and may advantageously be administered with or without food.

DETAILED DESCRIPTION OF THE INVENTION

In one aspect, the invention provides a formulation a lower concentration (in milligrams (mg) of spinosad per kilogram (kg) of body weight) of spinosad than is previously believed necessary for efficacy in controlling pests in and on animals.

In embodiments, the invention provides a single-dose oral formulation for controlling pests in an animal, such as controlling flea infestation, the formulation including spinosad and an insect growth regulator, such as lufenuron. The insect growth regulator may include one or more of lufenuron, fluazuron, milbomycin oxime, avermectin, diflubenzuron, teflubenzuron, chlorfluazuron, hexaflumuron, triflumuron, flufenoxuron and/or flucycloxuron. In one embodiment, the invention provides a formulation that includes spinosad and lufenuron, wherein the formulation is suitable for administration as an oral formulation to a dog.

In another aspect, the invention provides a lower concentration (in milligrams (mg) of spinosad per kilogram (kg) of body weight) of spinosad than is previously believed necessary for efficacy in controlling fleas without risk of emesis. In particular, the formulation of the invention provides 20 mg/kg of spinosad to 10 mg/kg of lufenuron for administration to a dog, versus the 30 mg/kg dose provided by the COMFORTIS® product.

In one embodiment, the invention provides a single-dose oral formulation for controlling a flea infestation on an animal including spinosad, lufenuron, microcrystalline cellulose, croscarmellose sodium, magnesium stearate, and optionally an artificial flavor. The formulation is suitable for oral administration once every 30 days at a dose of at least about 20 mg of spinosad per kg of body weight of the animal, and about 10 mg of lufenuron per kg of body weight of the animal.

Exemplary formulations of the invention are shown in Table I.

TABLE I

Formulation

| Ingredient | % w/w |
|---|---|
| Lufenuron (500 mg/g) Granulation | 30.67 |
| Spinosad (600 mg/g) Granulation | 37.78 |
| Spray Dried Liver Powder | 12.00 |
| Microcrystalline Cellulose (Heweten 102) | 14.80 |
| Croscarmellose Sodium (Ac-Di-Sol SD-711) | 3.00 |
| Colloidal Silicone Dioxide (Aerosil 200 Pharma) | 0.50 |
| Magnesium Stearate (Hyqual) | 1.25 |
| Total | 100.0 |

The single active ingredients may be prepared as follows:

| | % w/w |
|---|---|
| Lufenuron (500 mg/g) Granulation | |
| Polyethylene Glycol 8000 | 50.0 |
| Lufenuron Micronized | 50.0 |
| Total | 100.0 |
| Spinosad 60% w/w Granulation | |
| Spinosad | 60.0 |
| Lactose Monohydrate (Granulac 200) | 23.25 |
| Microcrystalline Cellulose (Heweten 101) | 7.75 |
| Povidone K-30 (Kollidon 30) | 7.00 |
| Croscarmellose Sodium (Ac-Di-Sol SD-711) | 2.00 |
| Purified Water | 25.38* |
| Total | 100.0* |

*Water is evaporated during the process and is not considered part of the total.

The actives can react to form physiologically acceptable derivatives or salts that are also useful in the methods and formulations of this invention. The salts can be prepared using standard procedures for salt preparation. The term "pharmaceutically acceptable salt" refers to an addition salt that exists in conjunction with the acidic or basic portion of spinosad and/or lufenuron. Such salts include the pharmaceutically acceptable salts listed in HANDBOOK OF PHARMACEUTICAL SALTS: PROPERTIES, SELECTION AND USE, P. H. Stahl and C. G. Wermuth (eds.), Wiley-VCH, New York, 2002 which are known to the skilled artisan. Pharmaceutically acceptable salts of an acid addition nature are formed when spinosad and any of its intermediates containing a basic functionality are reacted with a pharmaceutically acceptable acid. Pharmaceutically acceptable acids commonly employed to form such acid addition salts include inorganic and organic acids. Pharmaceutically acceptable salts of a base addition nature are formed when spinosad and any of its intermediates containing an acidic functionality are reacted with a pharmaceutically acceptable base. Pharmaceutically acceptable bases commonly employed to form base addition salts include organic and inorganic bases.

For example, spinosyn A can be neutralized with an appropriate acid to form an acid addition salt. The acid addition salts include salts formed by reaction with either an organic or inorganic acid such as, for example, sulfuric, hydrochloric, phosphoric, acetic, succinic, citric, lactic, maleic, fumaric, cholic, pamoic, mucic, glutamic, camphoric, glutaric, glycolic, phthalic, tartaric, formic, lauric, stearic, salicylic, methanesufonic, benzenesulfonic, sorbic, picric, benzoic, cinnamic, and like acids.

In addition to pharmaceutically acceptable salts, other salts are included in the present invention. They may serve as intermediates in the purification of compounds or in the preparation of other pharmaceutically-acceptable salts, or are useful for identification, characterization or purification.

In particular embodiments, spinosad is a natural product composed of spinosyn factors A and D, in normally a 17:3 ratio.

Systemic efficacy (ingestion of blood containing a formulation of the invention by the blood feeding parasites, such as fleas) provides different mode of exposure compared to topically applied ectoparasiticides where contact with the parasite at the skin surface is the mode of exposure. The advantages of oral systemic treatments and killing of parasites from ingestion of blood, compared to topical applications and contact killing, include: a) reduced exposure to the human applicator and children and objects in the animal's environment (e.g., flooring, carpets, furniture); b) no worry about loss from exposure of the animal to water (lakes, streams, bathing, etc.) or from loss due to rubbing; c) no concern about UV exposure and degradation; d) no problems with oxidation from oils on skin, etc.; and e) assurance that the entire dose is administered (compared to a topical application where some of the dose may drip off, rub off and/or remain in the dispensing tube immediately after treatment).

The formulations of this invention may further include, in combination with the spinosyn and lufenuron component, one or more other active compounds, including those that have activity against the fleas to be controlled, such as, for example, synthetic pyrethroids, natural pyrethins, organophosphates, organochlorines, carbamates, foramidines, avermectins, milbemycins, other insect growth regulators (including chitin synthesis inhibitors, juvenile hormone analogs, and juvenile hormones), nitromethylenes, pyridines and pyrazoles.

All ratios, percentages, and parts discussed herein are "by weight" unless otherwise specified.

The term "oral formulation" means that spinosad, either alone or in combination with one or more of the other types of compounds listed supra, is formulated into a product or formulation suitable for administering to the animal by mouth. These products or formulations include, but are not limited to, tablets, capsules, liquids, gels, pastes, oral sprays, buccal formulations, powders and chewable treats or animal feeds containing the active component or components. Generally, such formulations include a physiologically acceptable carrier. Such carriers are well known in the veterinary arts. Animal feeds and animal-accepted flavorings (e.g., natural or artificial meat flavors) are useful carriers to enhance palatability of the formulations. A compressible tablet is a particularly useful form of the oral formulation of the invention, as is a chewable tablet as manufactured, for example, in accord with the disclosure of U.S. Pat. No. 7,955,632, the contents of which are incorporated herein by this reference.

The term "controlling a flea infestation" refers to prevention of flea infestations (such as *C. felis*), treatment of flea infestations, or prevention and treatment of flea infestations. Furthermore, "controlling a flea infestation" includes preventing, minimizing or eliminating an infestation by fleas. In some embodiments, the fleas present at a stage selected from the group consisting of egg, larvae, and adult.

The term "single-dose formulation" means that one dose of the formulation effectively controls the flea infestation for a prolonged time. The term "prolonged time" comprises a according to the excipients added, but will be adjusted in accord with principles familiar to those of ordinary skill in the art to provide the requisite doses.

EXAMPLES

Examples of use of the invention follow in canines, where group 2 received no treatment and group 1 received the inventive formulation as described in Table I:

|  | Day 1 19 Aug. 2016 | | Day 21 8 Sep. 2016 | | Day 28 15 Sep. 2016 | | Day 35 22 Sep. 2016 | |
| --- | --- | --- | --- | --- | --- | --- | --- | --- |
| Group | Live | Dead | Live | Dead | Live | Dead | Live | Dead |
| 2 | 83 | 3 | 61 | 0 | 76 | 0 | 75 | 0 |
| 2 | 85 | 1 | 100 | 0 | 97 | 0 | 107 | 0 |
| 2 | 84 | 0 | 76 | 0 | 82 | 0 | 76 | 1 |
| 2 | 76 | 0 | 39 | 0 | 76 | 0 | 79 | 0 |
| 2 | 83 | 0 | 97 | 0 | 98 | 0 | 81 | 0 |
| 2 | 87 | 0 | 87 | 0 | 80 | 0 | 122 | 0 |
| 2 | 91 | 0 | 133 | 0 | 101 | 0 | 110 | 0 |
| 2 | 96 | 0 | 87 | 0 | 85 | 0 | 78 | 0 |
| 2 | 82 | 0 | 135 | 0 | 90 | 0 | 104 | 0 |
| 2 | 109 | 0 | 98 | 0 | 118 | 0 | 103 | 0 |
| 1 | 0 | 12 | 0 | 1 | 13 | 0 | 28 | 2 |
| 1 | 0 | 6 | 0 | 0 | 3 | 4 | 9 | 3 |
| 1 | 0 | 15 | 0 | 0 | 2 | 2 | 11 | 1 |
| 1 | 0 | 8 | 0 | 11 | 6 | 5 | 13 | 1 |
| 1 | 0 | 12 | 0 | 12 | 1 | 3 | 0 | 3 |
| 1 | 1 | 24 | 0 | 6 | 1 | 9 | 12 | 0 |
| 1 | 0 | 4 | 0 | 3 | 4 | 0 | 16 | 0 |
| 1 | 0 | 19 | 0 | 6 | 2 | 5 | 7 | 5 |
| 1 | 0 | 12 | 0 | 6 | 1 | 2 | 9 | 0 |
| 1 | 0 | 3 | 0 | 13 | 0 | 2 | 1 | 3 |
| Efficacy | 99.9% | | 100.0% | | 96.3% | | 88.7% | |

* Treatments administered on D 0, 100 Fleas were added at D −1, D 18, D 25, D 32 period of at least 30 days. The term "long-acting" means that the activity lasts for a prolonged time, for example a period of 35 days or 37 days. "Suitable for oral administration once every 30 days" means an oral administration which provides the requisite period of protection (at least about every 30 days) while maintaining the requisite efficacy, as defined below.

The formulations of the present invention comprise an effective amount of spinosad and lufenuron administered orally to the animal, such as a dog. The terms "effective amount" and "ectoparasiticidal amount" refer to the amount needed to control the flea infestation. As those in the art will understand, this amount will vary depending upon a number of factors. These factors include, for example, the breed of dog being treated, its weight, and general physical condition.

In general, an effective amount refers to a dose of about 20 mg of spinosad per kg of body weight of the dog in conjunction with about 10 mg of lufenuron per kg of body weight, or at a 2:1, 3:1 and has much as a 4:1 ratio. The term "about 20 mg of spinosad" and "about 10 mg of lufenuron" refers to a dose of the active ingredients which may vary by minor amounts, such as from 18 to 33 mg of spinosad/kg and 8 to 18 mg/kg of lufenuron. As such, a person of ordinary skill in the art would understand the range of doses encompassed by the term "about 20 mg" or about "10 mg" to be within the range of a 2:1 ratio of the spinosad to the lufenuron, varying according to the body weight and condition of the animal (e.g., the mg/kg range for smaller animals will be higher). In addition, the amounts of spinosad and lufenuron as w/w of the overall formulation will vary Emesis among the group 1 animals was zero throughout the study. The invention therefore provided comparable or greater efficacy to spinosad administered alone (e.g., as part of COMFORTIS®), without the emesis which spinosad and lufenuron are known to stimulate.

Although the objects of the disclosure have been described with reference to the above example, it will be understood that modifications and variations are encompassed within the spirit and scope of the disclosure. Accordingly, the disclosure is limited only by the following claims.

What is claimed is:

1. A method of controlling a flea infestation on an animal, comprising administering to the animal an effective amount of a single-dose oral formulation comprising spinosad, lufenuron, microcrystalline cellulose, croscarmellose sodium, and magnesium stearate, and optionally an artificial flavor, wherein the formulation is suitable for oral administration once every 30 days at a dose of at least about 20 mg of spinosad per kg of body weight of the animal, and about 10 mg of lufenuron per kg of body weight of the animal.

2. The method of claim 1, wherein the animal is a dog and the formulation has greater than about 75, 90 or 95% residual efficacy at 30 days post-administration.

3. A method of controlling a flea infestation on an animal, comprising administering to the animal an effective amount of a single-dose oral formulation per month, the formulation comprising spinosad and lufenuron at a dose of at least about 20 mg of spinosad per kg of body weight of the animal, and about 10 mg of lufenuron per kg of body weight of the animal.

4. The method of claim 3, wherein the animal is a cat.

5. The method of claim 3, wherein the animal is a dog.

6. The method of claim 3, wherein the animal is a domesticated dog.

7. The method of claim 3, wherein the formulation is a tablet or capsule.

8. The method of claim 3, wherein the formulation has greater than 75% residual efficacy at 30 days post-administration.

9. The method of claim 3, wherein the formulation has greater than 90% residual efficacy at 30 days post-administration.

10. The method of claim 3, wherein the formulation has greater than 95% residual efficacy at 30 days post-administration.

11. The method of claim 3, wherein the single-dose oral formulation is administered about every 30 days.

* * * * *